United States Patent
Swallow et al.

(10) Patent No.: US 6,767,746 B2
(45) Date of Patent: Jul. 27, 2004

(54) METHOD AND APPARATUS FOR ANALYZING ACID GAS LOADING WITHIN AN AMINE SOLUTION

(75) Inventors: Jamie Swallow, High River (CA); Brent Richmond Young, Calgary (CA)

(73) Assignee: Spartan Controls Ltd., Calgary (CA)

(*) Notice: Subject to any disclaimer, the term of this patent is extended or adjusted under 35 U.S.C. 154(b) by 226 days.

(21) Appl. No.: 09/919,331

(22) Filed: Jul. 30, 2001

(65) Prior Publication Data

US 2003/0022386 A1 Jan. 30, 2003

(51) Int. Cl.[7] ................................................ G01N 33/00
(52) U.S. Cl. .................... 436/121; 436/61; 436/100; 436/133; 436/149; 436/150; 436/178; 422/82.01; 422/82.02
(58) Field of Search .................. 436/121, 61, 100, 436/133, 149, 150, 178, 111–112, 55, 163, 120, 139, 102; 422/82.02, 68.1, 80, 75, 76, 77; 423/229, 226, 228

(56) References Cited

U.S. PATENT DOCUMENTS

| | | | | |
|---|---|---|---|---|
| 4,113,849 A | * | 9/1978 | Atwood | 423/574.1 |
| 4,795,565 A | * | 1/1989 | Yan | 210/669 |
| 4,801,551 A | * | 1/1989 | Byers et al. | 436/133 |
| 4,814,281 A | * | 3/1989 | Byers | 436/150 |
| 5,162,084 A | * | 11/1992 | Cummings et al. | 210/662 |
| 5,292,407 A | * | 3/1994 | Roy et al. | 205/431 |
| 5,368,818 A | * | 11/1994 | Cummings et al. | 422/62 |
| 5,547,648 A | * | 8/1996 | Buchanan et al. | 423/210 |
| 5,994,147 A | * | 11/1999 | Rodriguez et al. | 436/163 |
| 6,071,484 A | * | 6/2000 | Dingman, Jr. et al. | 423/229 |
| 6,245,128 B1 | * | 6/2001 | George, Jr. | 95/186 |
| 6,517,700 B2 | * | 2/2003 | Byszewski | 205/431 |

* cited by examiner

Primary Examiner—Jill Warden
Assistant Examiner—Sam P. Siefke
(74) Attorney, Agent, or Firm—John Russell Uren

(57) ABSTRACT

Method and apparatus used to calculate the hydrogen sulfide and carbon dioxide loading of both rich and lean amine solutions used to remove acidic gas components from sour or production gases in order to produce a sweet or sales gas for transmission purposes. The amine solution is divided into three (3) liquid streams carrying different proportions of heat stable salts, hydrogen sulfide and carbon dioxide. Conductivity measurements are made on each of the streams and are converted to acid loading values for the amine. The acid loading values of the amine are used to obtain the hydrogen sulfide and carbon dioxide loading for the amine solution.

7 Claims, 2 Drawing Sheets

METHOD AND APPARATUS FOR ANALYZING ACID GAS LOADING WITHIN AN AMINE SOLUTION

INTRODUCTION

This invention relates to acid gas loading within an amine solution and, more particularly, to determining hydrogen sulfide ($H_2S$) and carbon dioxide ($CO_2$) loading within the amine solution by utilising liquid conductivity to determine the loading of the hydrogen sulfide and carbon dioxide.

BACKGROUND OF THE INVENTION

Contracts are entered between the sellers or producers of natural gas and the transmission companies who transport such gas within their pipelines. These contracts specify the parameters of the gas sold by the producers that will be transported within the pipelines of the transmission companies. The prices for transportation of such gases are based on the specifications and, indeed, the gas eventually transported within the pipeline is required to fall within appropriate limit parameters.

Sweet or sales gas is carried by the pipelines. This gas is the originally produced sour gas which has had a certain percentage of hydrogen sulfide and carbon dioxide removed. The sour gas emanates from the producing formation of the oil or gas well. It is transported to an absorber containing an amine solution. The acid gases chemically react with the amine and are removed in their liquid form. This so called "sweet gas" from the absorber is subsequently dehydrated and sold to the transmission company.

The hydrogen sulfide and carbon dioxide removed from the sour gas leave the absorber within a "rich" amine solution which has a relatively high concentration of the acid hydrogen sulfide and carbon dioxide. This rich amine solution is introduced into a regenerator or stripper and a reboiler. As the rich amine flows through the regenerator and reboiler, the hydrogen sulfide and carbon dioxide is stripped from the amine. The resulting "lean" amine containing relatively low concentrations of hydrogen sulfide and carbon dioxide is recirculated back into the absorber where it is reused on the sour gas flowing into the absorber as just described.

A parameter that is important for controlling the reversible reaction both in the absorber or contactor and the stripper or regenerator is the concentration measurement or the "loading" of the hydrogen sulfide and carbon dioxide in both the lean and rich amine solutions. In respect of the lean amine loading calculation, a feed forward indication is provided to the absorber which is used to calculate the quantity of lean amine solution which must be provided to the absorber so the appropriate quantity of acid gas is removed from the sour natural gas and to ensure the sweet or sales gas meets the pipeline specifications. Lean amine calculations further provide a feed back indication of how efficiently the regenerator is stripping the acid gas from the rich amine liquid. In respect of rich amine liquid, a feed forward indication for the calculation is provided which will provide the quantity of energy necessary within the regenerator/reboiler to strip the acid gas from the rich amine liquid.

Heretofore, the measurement for amine loading of the amine solution used to remove the acid gases from the production sour gas was obtained by driving the acid gas components of the liquid amine into the gaseous phase and then analysing the gases. An ultraviolet gas analyzer was used for the hydrogen sulfide and an infrared analyser was used for the carbon dioxide. The results of the two analyzers were expressed as a concentration measurement, conveniently parts per million (ppm) or grains/gallon.

While this technique has certain advantages such as confining the concentration measurements to the two specific gases, namely carbon dioxide and hydrogen sulfide, and thereby avoiding interference with any other gases in the gas stream, the use of two analyzers is expensive, there is a large lag time to obtain the measurement because of the phase change requirement and the maintenance costs for two analyzers and their associated components are high.

SUMMARY OF THE INVENTION

According to one aspect of the invention, there is provided a method for determining the acid concentration of an amine solution carrying hydrogen sulfide and carbon dioxide comprising the steps of determining the conductivity of a first liquid stream containing said hydrogen sulfide, said carbon dioxide and heat stable salts in said amine solution; removing significantly all of said heat stable salts from said first liquid stream to form a second liquid stream; determining the conductivity of said second liquid stream containing said hydrogen sulfide and said carbon dioxide without said heat stable salts; removing significantly all of said hydrogen sulfide from said second liquid stream to form a third liquid stream; determining the conductivity of said third liquid stream containing said carbon dioxide without said hydrogen sulfide; and analysing said conductivity measurements of said first, second and third liquid streams to obtain said acid gas loading of said amine solution.

According to a further aspect of the invention, there is provided, apparatus for determining the acid concentration of an amine solution carrying hydrogen sulfide and carbon dioxide comprising a first analytical cell for measuring the conductivity of a first liquid stream containing said hydrogen sulfide, said carbon dioxide and heat stable malts within said amine solution, a second analytical cell for measuring the conductivity of said second liquid stream containing said hydrogen sulfide and carbon dioxide without said heat stable salts, a hydrogen sulfide remover for acting on said second liquid stream and removing said hydrogen sulfide thereby to form a third liquid stream, a third analytical cell for measuring the conductivity of said third liquid stream containing said carbon dioxide without said hydrogen sulfide and said heat stable salts and a computing device operable to receive signals from said first, second and third analytical cells, to analyse said measurements of said conductivity of said first, second and third analytical cells and to produce a value for said acid concentration of said amine solution.

BRIEF DESCRIPTION OF THE SEVERAL VIEWS OF THE DRAWINGS

Specific embodiments of the invention will now be described, by way of example only, with the use of drawings in which.

DESCRIPTION OF SPECIFIC EMBODIMENT

Figure 1:
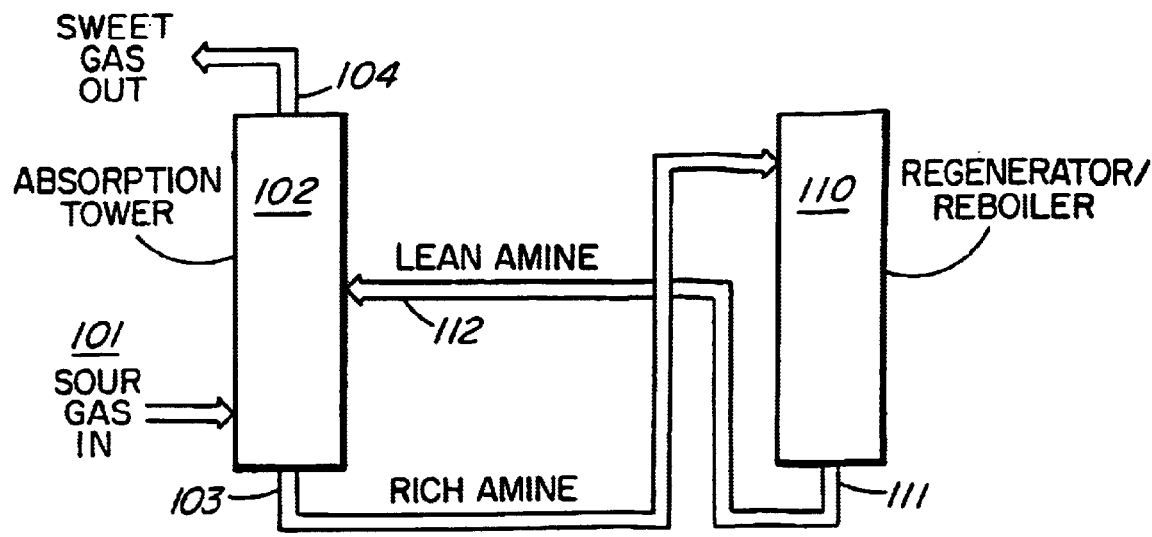
FIG. 1 illustrates the removal of acid gases from sour gas in an absorption tower and the recirculation of lean amine to the absorption tower according to the PRIOR ART.

Referring now to the drawings, the apparatus used generally for the removal of the acidic gas components of a sour gas production flow and the recirculation of amine according to the prior art is shown generally at 100 in FIG. 1. The production or sour gas 101 is flowed into an absorption tower 102 carrying an amine solution. The acidic gas components, principally hydrogen sulfide (H2S) and carbon dioxide (CO2), react with the amine solution and enter into the solution thereby creating a "rich" amine solution with high concentrations of hydrogen sulfide and carbon dioxide, which rich amine leaves the absorption tower 102 at 103. "Sweet" or sales gas without the acidic components leaves the absorption tower 102 at line 104. The sweet gas is dehydrated and sold to a transmission company for transportation to markets.

The rich amine solution in line 103 is introduced to a regenerator/reboiler 110. The hydrogen sulfide and carbon dioxide are "stripped" from the amine as the solution flows downwardly within the regenerator/reboiler 110 and the "lean" amine without significant concentrations of hydrogen sulfide and carbon dioxide leaves the regenerator/reboiler 110 at 111 and is reintroduced into absorption tower 102 through line 112. The technique described is commonly used in the PRIOR ART and forms no part of the present invention.

In order to obtain the necessary quantity of lean amine for use in the absorption tower 112, the hydrogen sulfide and carbon dioxide concentration or "loading" of the amine solution is required for both the rich amine leaving absorption tower 112 and the lean amine being reintroduced into absorption tower 102 from regenerator/reboiler 110. These figures are required for several purposes. First, the concentration is required so as to provide an indication of the quantity of lean amine solution that must be circulated into the absorption tower 102 to remove the necessary acid components from the sour gas of the production well so as to meet pipeline specifications and transmission contracts. Second, the concentration of the lean amine gives an indication of the operating efficiency of the regenerator/reboiler 110 in removing the acid gas components from the rich amine solution. Third, the concentration of acidic components in the rich amine solution provides a feed forward indication of the energy that will be required within the regenerator/reboiler 110 to strip the acid gases from the rich amine.

Figure 2:
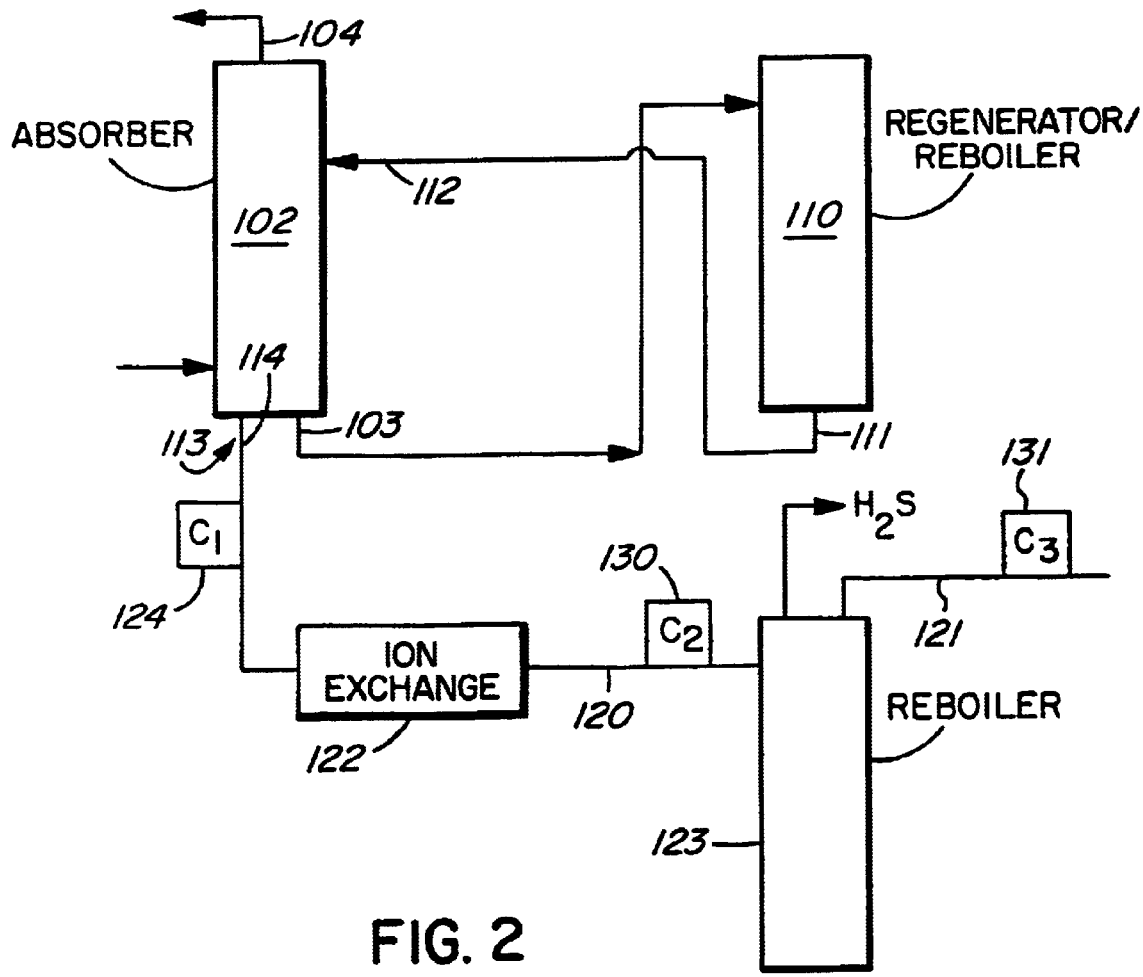
FIG. 2 illustrates the measurement of conductivity of a first, second and third liquid stream carrying hydrogen sulfide and carbon dioxide according to the invention.

Reference is now made to FIG. 2 which illustrates the method and apparatus conveniently used according to the invention. The process of FIG. 1 continues; that is, the rich amine leaves the absorption tower 102 at 103 and is directed to the regenerator/reboiler 110 where the hydrogen sulfide and carbon dioxide components are removed and the lean amine exiting from the regenerator/reboiler 110 is reintroduced into absorber 102 at 112 as has been described. However, a further liquid stream 113 is created which uses the rich amine leaving the absorption tower 102 and within which the degradation product of heat stable salts (HSS) are of interest.

Liquid stream 113 is conveniently divided, for description purposes, into three different streams, namely first liquid stream 114 extending from absorption tower 102 to a heat stable salt remover 122, conveniently an ion exchange bed, second liquid stream 120 which extends from the ion exchange bed 122 to a reboiler 123 wherein the hydrogen sulfide is removed from the rich amine and third liquid stream 121 which carries the amine solution now only with the carbon dioxide acid gas components.

Three (3) analytical cells 124, 130, 131 are provided for measuring the conductivity of each of the first, second and third liquid streams 114, 120, 121, respectively; that is, the conductivity of the rich amine containing the heat stable salts, the hydrogen sulfide and the carbon dioxide is measured by first analytical cell 124; the conductivity of the rich amine with the heat stable salts removed and thereby forming the second liquid stream 120 is measured at second analytical cell 130; and the conductivity of the rich amine with the heat stable salts and the hydrogen sulfide removed and thereby forming the third liquid stream 121 is measured at third analytical cell 131. These conductivity measurements are used to determine the rich and lean amine loading as will be described.

Operation

Figure 3A:
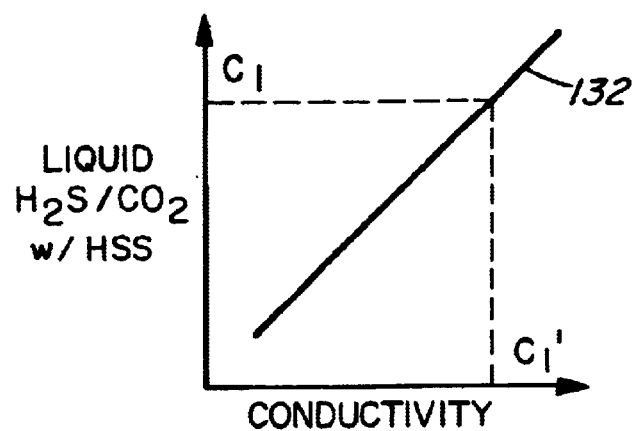
FIGS. 3A, 3B and 3C illustrate the conductivity measurements for each of the first, second and third liquid streams according to the invention.
Figure 3B:
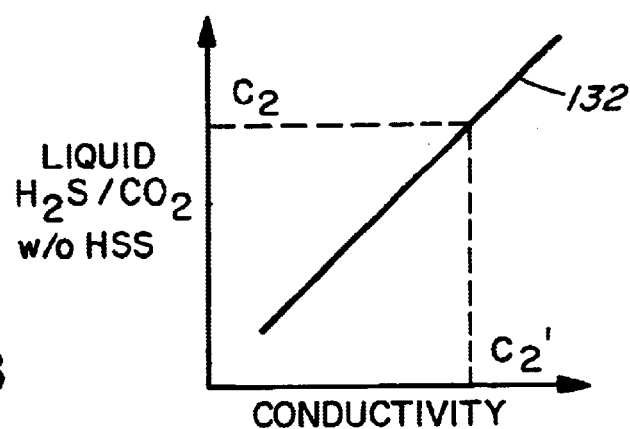
Figure 3C:
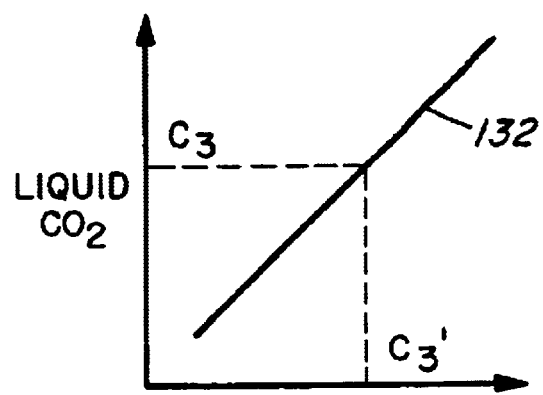

In operation, the conductivity measurements taken at each of the analytical cells 124, 130, 131 will be used to calculate the lean and rich amine loading and reference therein is now made to FIGS. 3A–3C.

In general, the slope of the line 132 is known for all of the first, second and third liquid streams 114, 120, 121; that is, as the concentration of the conductive heat stable salts, carbon dioxide and hydrogen sulfide within the amine increases, the conductivity will also increase and the positioning and slope of line 132 is obtained by iterative graphing prior to the conductivity calculations so that the line 132 is in a known position on the three graphs illustrated. A first conductivity measurement, C1', is obtained from first analytical cell 124 for the first liquid stream 114. By contact with slope 132 to obtain an appropriate ordinate value, a figure C1 is obtained for the loading of first liquid stream 114 which is carrying the hydrogen sulfide, the carbon dioxide and the heat stable salts. Likewise, the second conductivity measurement, C2', is obtained from second analytical cell 130 on the liquid stream 120 in which the heat stable salts have been removed by ion exchange bed 122. The second conductivity measurement will give a figure C2 for the loading of the second liquid stream 120 but which liquid stream has the heat stable salts removed. Similarly, a third conductivity measurements C3' is obtained for the loading of the third liquid stream 121 by third analytical cell 131 and, by similar technique, a value C3 is obtained for the loading of the third liquid stream 121 but which stream only carries carbon dioxide in the amine, the hydrogen sulfide having been substantially removed by passing the solution through reboiler 123 where the hydrogen sulfide is stripped from the amine and vented from reboiler 123.

By utilising the figures C1, C2 and C3, the hydrogen sulfide gas loading may be obtained as follows:

Total acid gas loading=C1−C2     (1)

Carbon dioxide loading=C3     (2)

therefore:

Hydrogen sulfide loading=(C1−C2)−C3     (3)

It can therefore be seen that the use of conductivity measurements as taken on three different liquid streams will give the loading quantities of the carbon dioxide and hydrogen sulfide components of an amine solution which is useful for processing purposes in producing the sweet or sales gas from production or sour gas in the liquid phase thereby removing the necessity of converting the liquid components of acid gases to the gaseous phase which reduces response time. It is also beneficial that gas analyzers with their concomitant maintenance requirements are not necessary and the calculation of the factors C1, C2 and C3 from the conductivity measurements are obtained through well proven technology in other liquid analytical applications.

While the calculation of the amine loading has been given with respect to graphical techniques which are carried out manually according to the invention, it is, of course, quite clear that the values could be obtained by way of appropriate transducers or other sensors which provide information to a computing device, a controller and/or an associated microprocessor or the like thereby allowing an automatic calculation of the conductivities and the acid gas loading which can also be used to adjust the processing parameters used to strip the rich amine and thereby form the lean amine for recirculation.

Further, while the invention has been specifically described as being particularly applicable to analysis of a rich amine solution, it is likewise applicable to lean amine solutions.

Many modifications will readily occur to those skilled in the art to which the invention relates and the specific embodiments described should be taken as illustrative of the invention only and not as limiting its scope as defined in accordance with the accompanying claims.

We claim:

1. Method for determining the acid concentration of an amine solution carrying hydrogen sulfide and carbon dioxide received from sour gas comprising the steps of determining the conductivity of a first liquid stream containing said hydrogen sulfide, said carbon dioxide and heat stable salts in said amine solution; removing significantly all of said heat stable salts from said first liquid stream to form a second liquid stream; determining the conductivity of said second liquid stream containing said hydrogen sulfide and said carbon dioxide without said heat stable salts; removing significantly all of said hydrogen sulfide from said second liquid stream to form a third liquid stream; determining the conductivity of said third liquid stream containing said carbon dioxide without said hydrogen sulfide and said heat stable salts; and analysing said conductivity measurements of said first, second and third liquid streams to obtain said acid gas loading of said amine solution.

2. Method as in claim 1 wherein said amine solution is a rich amine solution.

3. Method as in claim 1 wherein said amine solution is a lean amine solution.

4. Apparatus for determining the acid concentration of an amine solution carrying hydrogen sulfide and carbon dioxide received from sour gas comprising a first analytical cell for measuring the conductivity of a first liquid stream containing said hydrogen sulfide, said carbon dioxide and heat stable salts within said amine solution, a second analytical cell for measuring the conductivity of said second liquid stream containing said hydrogen sulfide and said carbon dioxide without said heat stable salts, a hydrogen sulfide remover for acting on said second liquid stream and removing said hydrogen sulfide thereby to form a third liquid stream, a third analytical cell for measuring the conductivity of said third liquid stream containing said carbon dioxide without said hydrogen sulfide and said heat stable salts and a computing device operable to receive signals from said first, second and third analytical cells, to analyse said measurements of said conductivity of said first, second and third analytical cells and to produce a value for said acid concentration of said amine solution.

5. Apparatus as in claim 4 wherein said heat stable salt remover is an ion exchange bed.

6. Apparatus as in claim 5 wherein said hydrogen sulfide remover is a reboiler.

7. Apparatus as in claim 6 wherein said computing device is a controller or a microprocessor.

* * * * *